United States Patent
Nitz et al.

(10) Patent No.: US 9,868,699 B2
(45) Date of Patent: Jan. 16, 2018

(54) PROCESS FOR REMOVING CATIONS FROM AN ISOPHORONENITRILE PRODUCT MIXTURE

(71) Applicants: Joerg-Joachim Nitz, Essen (DE); Stephan Kohlstruk, Gladbeck (DE); Robert Jansen, Bottrop (DE); Andreas Merkel, Recklinghausen (DE); Anja Mueller, Dortmund (DE); Jan Cassens, Recklinghausen (DE); Axel Hengstermann, Senden (DE)

(72) Inventors: Joerg-Joachim Nitz, Essen (DE); Stephan Kohlstruk, Gladbeck (DE); Robert Jansen, Bottrop (DE); Andreas Merkel, Recklinghausen (DE); Anja Mueller, Dortmund (DE); Jan Cassens, Recklinghausen (DE); Axel Hengstermann, Senden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/075,976

(22) Filed: Mar. 21, 2016

(65) Prior Publication Data
US 2016/0272580 A1 Sep. 22, 2016

(30) Foreign Application Priority Data
Mar. 19, 2015 (EP) .................................. 15159843

(51) Int. Cl.
| | | |
|---|---|---|
| *C07C 253/34* | (2006.01) |
| *C07C 253/10* | (2006.01) |
| *B01J 39/20* | (2006.01) |
| *B01J 47/02* | (2017.01) |
| *B01J 31/02* | (2006.01) |
| *B01J 31/40* | (2006.01) |
| *B01J 47/026* | (2017.01) |

(52) U.S. Cl.
CPC ......... *C07C 253/34* (2013.01); *B01J 31/0212* (2013.01); *B01J 31/4015* (2013.01); *B01J 39/20* (2013.01); *B01J 47/026* (2013.01); *C07C 253/10* (2013.01); *C07C 2601/16* (2017.05); *Y02P 20/584* (2015.11)

(58) Field of Classification Search
CPC ... C07C 255/46; C07C 253/10; C07C 253/34; C07C 2601/16; B01J 31/0212; B01J 31/4015; B01J 39/20; B01J 47/026
See application file for complete search history.

(56) References Cited

U.S. PATENT DOCUMENTS
6,037,381 A 3/2000 Beer et al.

FOREIGN PATENT DOCUMENTS
| | | |
|---|---|---|
| DE | 197 58 296 A1 | 7/1999 |
| JP | 2000-336164 A | 12/2000 |
| JP | 2001-11173 A | 1/2001 |

*Primary Examiner* — Valerie Rodriguez-Garcia
(74) *Attorney, Agent, or Firm* — Oblon, McClelland, Maier & Neustadt, L.L.P.

(57) ABSTRACT

Cations are removed from a substance stream that is produced during the production of isophoronenitrile with the help of a cation exchanger.

18 Claims, 2 Drawing Sheets

PROCESS FOR REMOVING CATIONS FROM AN ISOPHORONENITRILE PRODUCT MIXTURE

BACKGROUND OF THE INVENTION

Field of the Invention

The present invention disclosure relates to the removal of cations from a substance stream produced during the production of isophoronenitrile with the help of a cation exchanger.

Discussion of the Background

The base-catalyzed reaction of hydrocyanic acid (HCN) with alpha,beta-unsaturated cyclic (or acyclic) ketones is a known reaction (Hydrocyanation of Conjugated Carbonyl Compounds, CHAPTER 3, Wataru Nagata and Mitsuru Yoshioka, Wiley 2005).

EP 2 721 002 discloses numerous processes for the preparation of isophoronenitrile, see the documents cited therein.

EP 2 649 043 describes a process for the preparation of isophoronenitrile. For the removal of the catalyst, the following documents are cited:

According to JP 06065182, after the reaction of HCN with IP has been carried out, the alkaline catalyst can be neutralized and the reaction mixture worked up directly in the distillation.

Alternatively, according to JP 06065183, the alkaline reaction mixture can be mixed with an inert solvent and worked up in a thin-film evaporator. This removes the catalyst, the high boilers and the solvent. The resulting isophoronenitrile is then purified in a further column.

The catalyst can be removed, for example, by the processes described in DE 10 85 871 or EP 433 615.

Isophoronenitrile (IPN) is produced by the reaction of isophorone (IP) with hydrocyanic acid with the assistance of a catalyst. Preferably, homogeneous base catalysis is used, for this alkali metal alcoholates, in particular sodium methanolate, are used as catalyst, as described in EP 2649043.

SUMMARY OF THE INVENTION

It was an object to improve the work-up of the resulting reaction mixture from the preparation of isophoronenitrile from isophorone and hydrocyanic acid.

The present invention relates to a process for removing a cation from an isophoronenitrile product mixture, said process comprising:

removing said cation from said isophoronenitrile product mixture, to obtain a purified product;
  wherein said isophoronenitrile product mixture is from the preparation of isophoronenitrile from isophorone and hydrocyanic acid in the presence of a cation-containing catalyst in homogeneous phase;
  wherein said cation is from the cation-containing catalyst;
  wherein said removing of the cation of the catalyst takes place by an ion exchanger without prior neutralization of the catalyst.

DETAILED DESCRIPTION OF THE INVENTION

Figure 1:
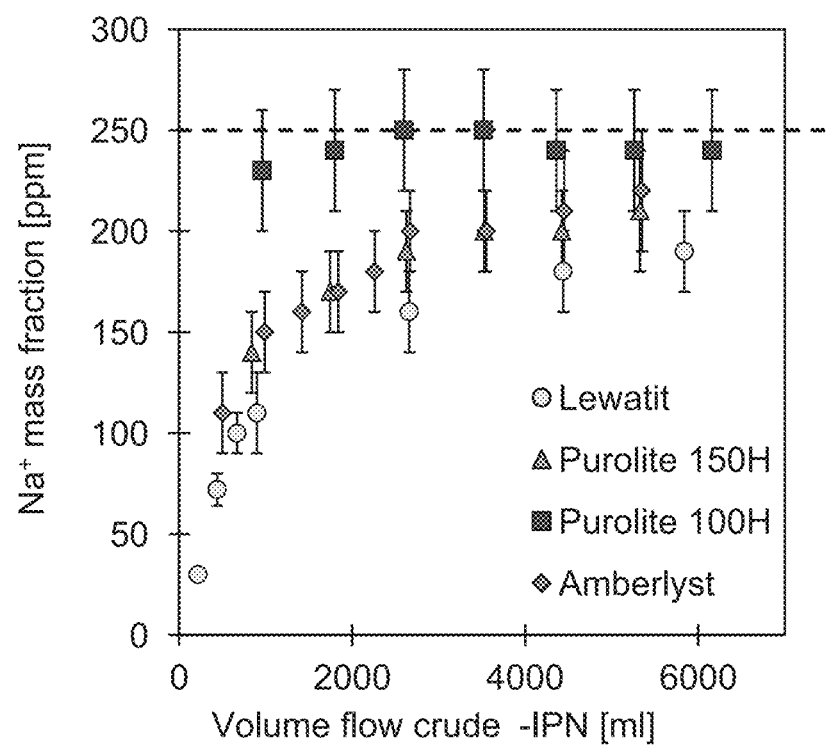
FIG. 1 compares the breakthrough curves of the sodium of the different ion exchangers for a crude isophoronenitrile volumetric flow rate of 15 ml/min. Dotted line: Sodium fraction in the feed.

The ranges below include all values and subvalues between the lower and higher limit of the range.

Surprisingly, it was found that as a result of using a cation exchanger the cations of the catalyst used can be removed and the amount of water used in the process can be greatly reduced, with the downstream purification of the isophoronenitrile being greatly simplified as a result. Likewise, the process step that the alkaline catalyst has to be neutralized before its removal is omitted.

The invention provides a process for removing cations from an isophoronenitrile product mixture from the preparation of isophoronenitrile from isophorone and hydrocyanic acid in the presence of a cation-containing catalyst in homogeneous phase, characterized in that the removal of the cations of the catalyst takes place by means of ion exchangers without prior neutralization of the catalyst.

The removal of the cations takes place in an ion exchanger apparatus which can be designed to be either single-stage or multi-stage. Preferably, the removal takes place in a single-stage in only one ion exchanger apparatus.

To prepare isophoronenitrile, isophorone and hydrocyanic acid are reacted according to the invention, with the reaction being carried out in the presence of a cationic catalyst.

The reaction is carried out according to the invention under homogeneous base catalysis. In the case of homogeneous catalysis, catalyst and reactants are present in the same phase, i.e. in homogeneous phase. Preferably, the catalyst is a metal salt dissolved in a solvent over which the reactants react to give the product isophoronenitrile.

The catalysts used in the process according to the invention are preferably soluble catalysts from the group of basic alkali metal or alkaline earth metal compounds. For this purpose, preference is given to using alkali metal alcoholates, in particular sodium methanolate, as catalysts.

According to the invention, preference is given to using a 20-35% strength by weight sodium methanolate solution, particularly preferably a 25-30% strength by weight sodium methanolate solution, dissolved in methanol.

The hydrocyanic acid used can be used in pure form or else as a mixture with stabilizers. Suitable stabilizers are all compounds known to the person skilled in the art for this purpose, for example phosphoric acid, sulfur dioxide and oxalic acid.

Preference is given to using phosphoric acid, sulfur dioxide or mixtures thereof as stabilizers for the hydrocyanic acid. The fraction of stabilizers is usually in the range from 0.1 to 2% by weight, based on the hydrocyanic acid used, preferably in the range from 0.5 to 1% by weight.

The reaction can be performed in the presence or absence of inert solvents. Particular preference is given to using isophorone in a molar excess, based on the hydrocyanic acid used, and to not adding any external solvent.

Generally, the process according to the invention is performed in such a way that an excess of isophorone is used, since a higher selectivity for isophoronenitrile is thus achieved. In general, the molar isophorone/HCN ratio is >1:1, generally 19:1 to 1.5:1, preferably 3:1 to 1.5:1.

The catalyst concentration, based on the amount of isophorone used, is in the range from 0.03 to 20% by weight, preferably in the range from 0.03 to 1% by weight.

The total amount of the isophorone can be initially charged and brought to the desired reaction temperature, before the HCN is added in the presence of the catalyst.

The HCN is preferably metered in such a way that a homogeneous distribution of the reactants (isophorone and HCN) is ensured. The metered addition of HCN is accomplished in a customary manner known to those skilled in the art, for example by means of static mixers, pumps or atomization.

The reaction temperatures are usually in the range from 130 to 225° C., preferably in the range from 135 to 195° C. and very particularly preferably in the range from 140 to 175° C.

The reaction is performed at pressures of 0.01 to 10 bar, preferably 1 to 5 bar, particularly preferably at standard pressure (atmospheric pressure).

Within the above-detailed reaction parameters, the HCN is metered in so as to result in a sufficiently low concentration of HCN, and a high selectivity and a high conversion to isophoronenitrile can thus be achieved. The selectivity with respect to IPN should be >95%, preferably >98%, particularly preferably >99%.

In the course of this, only a low level of polymerization of the HCN may occur, since this would adversely affect the conversion and selectivity.

Preferably, the concentrations of unconverted, free HCN and the total concentration of cyanide ions (sum of free HCN and cyanide bound in the form of cyanohydrins of isophorone and isophoronenitrile) are determined and the reaction conditions are adjusted so as to obtain an optimized selectivity with respect to IPN. Said cyanide ion concentrations are preferably determined by titration.

The process according to the invention, in a preferred manner, can be performed continuously, discontinuously or semicontinuously, especially continuously.

In a preferred embodiment, the reaction procedure, according to the catalyst used, is performed in a stirred tank, a stirred tank cascade, a circulation reactor, a flow tube, one or more fixed bed reactors or a column.

The work-up of the reaction mixture which, after the reaction has finished, comprises essentially the end product isophoronenitrile, but can also still comprise fractions of starting materials such as isophorone, HCN and also solvents and by-products, and comprises the catalyst, takes place according to the invention firstly by removing the cations from the catalyst over a cation exchanger without prior neutralization of the catalyst.

In principle, all cation exchangers can be used. Particular preference is given to immobilized ion exchangers which have, as functional groups, sulfonic acid groups which have been applied to a polystyrene matrix crosslinked with divinylbenzene.

The removal of the cations of the catalyst without its neutralization, in particular of the preferred sodium methanolate, takes place as the first purification step after the reactor. In this connection, the reaction product is conveyed over cation exchangers immobilized in one or more adsorption columns. The cations contained in the reaction mixture, in particular the sodium ions, are exchanged for hydrogen ions of the ion exchanger. As a result, the cation, in particular sodium, is removed from the product stream.

The removal of the cations takes place here without the addition of further chemical additives.

According to the invention, preference is given to using, as catalyst, sodium methanolate dissolved in methanol, where the methanolate is converted to methanol by exchanging the sodium ions for hydrogen ions of the ion exchanger. The product stream produced in this way comprises, compared to the customary process, less water, preferably no water, as a result of which the further purification steps are simplified.

Following removal of the cations of the catalyst, the resulting substance mixture is further worked-up by customary processes and then the isophoronenitrile is isolated as end product.

Preferably, the further work-up of the substance mixture after the ion exchange apparatus takes place according to the invention by the two variants described below.

For the purification of the water used in the neutralization, an additional column is necessary according to the prior art. In the process according to the invention, this column is significantly smaller or is omitted entirely. This establishes further technical progress.

In the first variant, the removal of the low boilers, according to the invention preferably methanol, takes place in a first column downstream of the ion exchanger. This column can be significantly smaller compared to the process with neutralization since the amount of low boilers to be separated off is significantly reduced. In a second downstream column, the purification of the isophoronenitrile then takes place. The high boilers leave the column at the bottom, isophorone leaves overhead and the isophoronenitrile is obtained in pure form at the side.

In the second variant, the purification of the substance mixture after the ion exchange apparatus is carried out in a downstream column which contains a partial condenser placed on top or within the column. In this connection, the removal of low boilers, isophorone and the high boilers is combined in only one column downstream of the ion exchanger. For this, the top stream in the column is only partially condensed by a contained partial condenser in order to separate the isophorone from low boilers, according to the invention preferably methanol. The high boilers leave the column at the bottom and the isophoronenitrile is obtained in pure form at the side.

In one embodiment, low boilers comprise methanol, isophorone, water, and HCN.

In one embodiment, high boilers comprise the condensation products of isophorone and isophorone nitrile with 2 or more rings.

Having generally described this invention, a further understanding can be obtained by reference to certain specific examples which are provided herein for purposes of illustration only, and are not intended to be limiting unless otherwise specified.

EXAMPLES

1.

In order to investigate the adsorptive removal of sodium from crude isophoronenitrile, experiments were carried out on the laboratory scale. For this, a double-walled glass column with an internal diameter of 20 mm was used. This was charged with the ion exchanger, the crude isophoronenitrile was preheated to 70° C. via a pump and placed on the top of the ion exchanger such that the isophoronenitrile was conveyed through the column under the force of gravity.

For the experiments, crude isophoronenitrile, essentially comprising:
isophoronenitrile, isophorone, high boilers, methanol, sodium methanolate, from a production plant was used. The following ion exchangers were tested:
Lewatit K2629 (Lanxess)
PPC 100H (Purolite)
PPC 150H (Purolite)
Amberlyst 15 WET (DOW)

All of the selected ion exchangers have, as functional groups, sulfonic acid groups which have been applied to a polystyrene matrix crosslinked with divinylbenzene. FIG. 1 compares the breakthrough curves of the sodium of the different ion exchangers for a crude isophoronenitrile volumetric flow rate of 15 ml/min. Here, the sodium weight fraction in the discharge from the ion exchanger is plotted against the amount of crude isophorone used. Besides the breakthrough curves, the sodium weight fraction in the feed to the ion exchanger is shown as a dotted line. Until the end of the measurements, thus also only about 25% of the active hydrogen ions were able to be replaced by sodium ions. The first ascertained sodium ion concentration was already 30 ppm after only 220 ml of purified isophoronenitrile; here, however, only approx. 3% of the hydrogen ions had been exchanged.

2.

Figure 2:
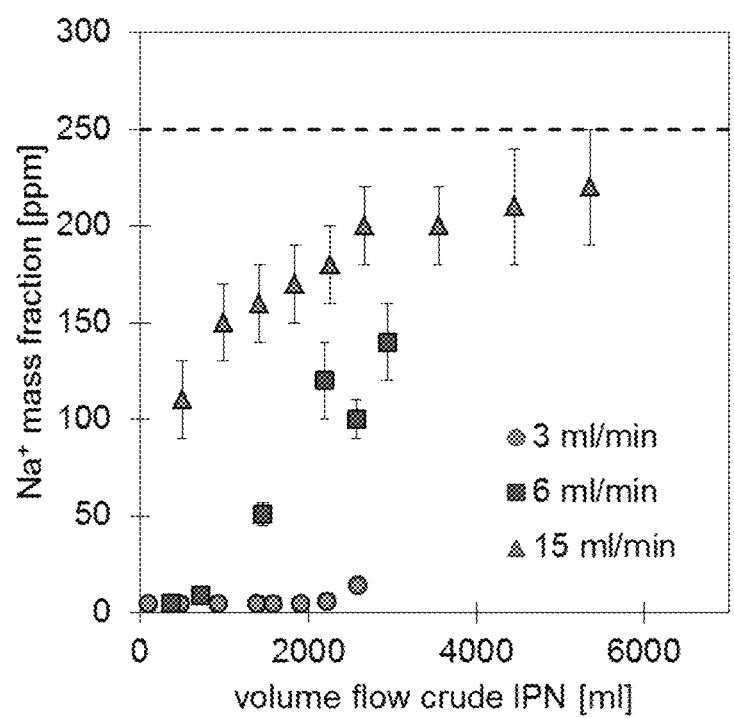
FIG. 2 compares the breakthrough curves of LEWATIT K2629 at different crude isophoronenitrile volumetric flow rates. Dotted line: Sodium fraction in the feed.

This is also confirmed by varying the volumetric flow rate under otherwise identical conditions for the cation exchanger Lewatit K2629. FIG. 2 compares the different volumetric flow rates. FIG. 2 reveals that the breakthrough curve shifts towards larger purified volumes the smaller the crude isophoronenitrile volumetric flow rate.

European patent application EP15159843 filed Mar. 19, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for removing a cation from an isophoronenitrile product mixture, said process comprising:
   exchanging a cation other than hydrogen in said isophoronenitrile product mixture with a hydrogen cation, to obtain a purified product;
      wherein said isophoronenitrile product mixture is from the preparation of isophoronenitrile from isophorone and hydrocyanic acid in the presence of a cation-containing catalyst in homogeneous phase in a reactor;
      wherein said cation is from the cation-containing catalyst;
      wherein said exchanging of the cation of the catalyst takes place by a cation exchanger without prior neutralization of the catalyst.

2. The process according to claim 1, wherein the exchanging of the cation takes place in a cation exchanger apparatus which is designed to be single-stage or multi-stage.

3. The process according to claim 1, wherein the exchanging of the cation takes place in a single-stage in only one cation exchanger apparatus.

4. The process according to claim 1, wherein said cation exchanger is an immobilized cation exchanger which has, as a functional group, a sulfonic acid group which has been applied to a polystyrene matrix crosslinked with divinylbenzene.

5. The process according to claim 1, wherein the exchanging of the cation of the catalyst takes place without neutralization of the catalyst, as first purification step after the reactor.

6. The process according to claim 2, wherein a further work-up of the substance mixture takes place after the cation exchange apparatus by removal of a low boiler in a first column downstream of the cation exchanger, and in a second downstream column the purification of the isophoronenitrile is then carried out.

7. The process according to claim 2, wherein a further purification of the isophoronenitrile after the cation exchange apparatus is carried out in a downstream column which contains a partial condenser placed on top or within the column.

8. The process according to claim 1, wherein the catalyst is a soluble catalyst selected from the group consisting of a basic alkali metal compound, a basic alkaline earth metal compound and mixtures thereof;
   wherein the catalyst is soluble in a solvent over which the reactants react to give the product isophoronenitrile.

9. The process according to claim 1, wherein the catalyst is an alkali metal alcoholate.

10. The process according to claim 1, wherein the catalyst is a 20-35% strength by weight sodium methanolate solution, dissolved in methanol.

11. The process according to claim 1, wherein the preparation of isophoronenitrile is carried out in the presence of an inert solvent.

12. The process according to claim 1, wherein a molar ratio isophorone/HCN is 19:1 to 1.5:1.

13. The process according to claim 1, wherein a catalyst concentration, based on the amount of isophorone used, is in the range from 0.03 to 20% by weight.

14. The process according to claim 1, wherein the preparation of isophoronenitrile is carried out in a stirred-tank, a stirred-tank cascade, a circulation reactor, a flow tube, one or more fixed-bed reactors or a column.

15. The process according to claim 6, wherein a low boiler is methanol.

16. The process according to claim 6, wherein a low boiler is selected from the group consisting of methanol, isophorone, water, HCN and mixtures thereof.

17. The process according to claim 1, wherein the catalyst is sodium methanolate.

18. The process according to claim 1, wherein the preparation of isophoronenitrile is carried out in the absence of an inert solvent.

* * * * *